(12) United States Patent
Chou et al.

(10) Patent No.: US 11,564,561 B2
(45) Date of Patent: Jan. 31, 2023

(54) WIRELESS CAMERA SYSTEM FOR ENDOSCOPE

(71) Applicant: Integrated Endoscopy, Inc., Irvine, CA (US)

(72) Inventors: David Chou, Irvine, CA (US); Siddharth Balvantrai Desai, Mission Viejo, CA (US)

(73) Assignee: INTEGRATED ENDOSCOPY, INC., Irvine, CA (US)

( * ) Notice: Subject to any disclaimer, the term of this patent is extended or adjusted under 35 U.S.C. 154(b) by 0 days.

(21) Appl. No.: 17/153,342

(22) Filed: Jan. 20, 2021

(65) Prior Publication Data

US 2021/0244265 A1 Aug. 12, 2021

Related U.S. Application Data

(60) Provisional application No. 62/966,464, filed on Jan. 27, 2020, provisional application No. 62/965,741, filed on Jan. 24, 2020.

(51) Int. Cl.
*H04N 9/47* (2006.01)
*A61B 1/05* (2006.01)
(Continued)

(52) U.S. Cl.
CPC .......... *A61B 1/053* (2013.01); *A61B 1/00016* (2013.01); *A61B 1/00034* (2013.01);
(Continued)

(58) Field of Classification Search
CPC .... A61K 31/16; A61K 31/325; A61K 31/365; A61K 39/3955; A61K 39/39558;
(Continued)

(56) References Cited

U.S. PATENT DOCUMENTS

D250,084 S  10/1978  Kirschensteiner
D292,227 S  10/1987  Rudelick
(Continued)

FOREIGN PATENT DOCUMENTS

CN   305308624      8/2019
JP   2012-055697 A  3/2012
(Continued)

OTHER PUBLICATIONS

International Search Report and Written Opinion dated May 14, 2021, received in International Patent Application No. PCT/US2021/014234, 13 pages.

(Continued)

*Primary Examiner* — Masum Billah
(74) *Attorney, Agent, or Firm* — Knobbe, Martens, Olson & Bear, LLP

(57) ABSTRACT

A wireless camera system includes a wireless camera for use in endoscopic procedures. The wireless camera can releasably couple with an endoscope (e.g., with a cordless disposable endoscope). The wireless camera can wirelessly transmit data to a controller, which can provide data output (e.g., snapshot images, video recording captured by the wireless camera) to an electronic display and to one or more data outputs (e.g., USB drive or other portable memory stick, to a remote computer or computer network, hard disk, compact flash drive, email, etc.).

19 Claims, 13 Drawing Sheets

(51) Int. Cl.
  *H04N 5/225* (2006.01)
  *H04N 7/18* (2006.01)
  *H04N 5/232* (2006.01)
  *A61B 1/00* (2006.01)

(52) U.S. Cl.
  CPC ...... *A61B 1/00066* (2013.01); *A61B 1/00121* (2013.01); *H04N 5/2252* (2013.01); *H04N 5/2253* (2013.01); *H04N 5/23216* (2013.01); *H04N 5/23299* (2018.08); *H04N 7/183* (2013.01); *H04N 2005/2255* (2013.01)

(58) Field of Classification Search
  CPC  A61K 45/06; A61B 1/00016; A61B 1/00034; A61B 1/00066; A61B 1/00121; A61B 1/042; A61B 1/053; H04N 2005/2255; H04N 5/2252; H04N 5/2253; H04N 5/2257
  See application file for complete search history.

(56) References Cited

U.S. PATENT DOCUMENTS

| | | |
|---|---|---|
| 4,782,819 A | 11/1988 | Adair |
| D325,857 S | 5/1992 | Hasegawa |
| D349,559 S | 8/1994 | Vanderhoef |
| D350,194 S | 8/1994 | Marino |
| D352,780 S | 11/1994 | Glaeser |
| D352,872 S | 11/1994 | Crockett |
| D353,888 S | 12/1994 | Raines |
| D396,624 S | 8/1998 | Basilius |
| 5,797,836 A | 8/1998 | Lucey |
| D409,563 S | 5/1999 | Haase |
| D436,118 S | 1/2001 | London |
| D436,165 S | 1/2001 | Donaldson |
| D436,819 S | 1/2001 | Liu |
| D437,539 S | 2/2001 | Kilmer |
| D441,834 S | 5/2001 | McGrath |
| D453,376 S | 2/2002 | McMahon |
| D454,951 S | 3/2002 | Bon |
| D466,213 S | 11/2002 | Snitkin |
| D471,578 S | 3/2003 | Okuley |
| D476,542 S | 7/2003 | Chunn |
| D478,986 S | 8/2003 | Johnston |
| D485,148 S | 1/2004 | Chen |
| D485,737 S | 1/2004 | Schaub |
| D486,370 S | 2/2004 | Chen |
| D486,713 S | 2/2004 | Lai |
| D487,219 S | 3/2004 | Chudy |
| D487,384 S | 3/2004 | Neitzel |
| D488,040 S | 4/2004 | Chen |
| D488,041 S | 4/2004 | Chen |
| D488,042 S | 4/2004 | Enck |
| D493,085 S | 7/2004 | Copeland, II |
| D497,786 S | 11/2004 | Concari |
| D498,400 S | 11/2004 | Wu |
| D508,458 S | 8/2005 | Solland |
| D508,835 S | 8/2005 | Schiller |
| D508,836 S | 8/2005 | Schiller |
| D509,119 S | 9/2005 | Schiller |
| D513,160 S | 12/2005 | DeBoer |
| D513,690 S | 1/2006 | Etter |
| D514,413 S | 2/2006 | Cuenca |
| D515,393 S | 2/2006 | Lin |
| D515,895 S | 2/2006 | Chen |
| D516,889 S | 3/2006 | Aglassinger |
| D516,890 S | 3/2006 | Huang |
| D521,927 S | 5/2006 | Franck |
| D524,133 S | 7/2006 | Wu |
| D524,282 S | 7/2006 | Beasley |
| D524,625 S | 7/2006 | Wu |
| D527,600 S | 9/2006 | Stratford |
| D530,818 S | 10/2006 | Lin |
| D531,000 S | 10/2006 | Meyers |
| D531,872 S | 11/2006 | Aglassinger |
| D531,873 S | 11/2006 | Liu |
| D532,666 S | 11/2006 | Chi |
| D542,618 S | 5/2007 | Miura |
| D545,427 S | 6/2007 | Gibson |
| D545,428 S | 6/2007 | Stammberger |
| D551,762 S | 9/2007 | Root |
| D565,920 S | 4/2008 | Bagley |
| D589,515 S | 3/2009 | Brunner |
| D597,392 S | 8/2009 | Meyers |
| D599,884 S | 9/2009 | Zore |
| D602,858 S | 10/2009 | Ellis |
| D604,844 S | 11/2009 | Summerer |
| D605,487 S | 12/2009 | Aglassinger |
| D605,488 S | 12/2009 | Aglassinger |
| D605,489 S | 12/2009 | Aglassinger |
| D606,827 S | 12/2009 | Fritz |
| D610,679 S | 2/2010 | Nakagawa |
| D625,058 S | 10/2010 | Kovach |
| D627,718 S | 11/2010 | Houghton |
| D628,290 S | 11/2010 | Romero |
| D653,206 S | 1/2012 | Heine |
| D657,646 S | 4/2012 | Schoch |
| D658,026 S | 4/2012 | Dale |
| D658,741 S | 5/2012 | Romero |
| D670,389 S | 11/2012 | Chen |
| D676,377 S | 2/2013 | Nokuo |
| D677,741 S | 3/2013 | Wilson |
| D677,830 S | 3/2013 | Daniels |
| D678,980 S | 3/2013 | Nies |
| D702,319 S | 4/2014 | Mammen |
| D702,648 S | 4/2014 | Ichio |
| D702,649 S | 4/2014 | Ichio |
| D706,980 S | 6/2014 | Tasar |
| D713,933 S | 9/2014 | Mammen |
| D713,934 S | 9/2014 | Mammen |
| D714,423 S | 9/2014 | Mammen |
| D714,908 S | 10/2014 | Mammen |
| D719,651 S | 12/2014 | Hoffmann |
| D735,133 S | 7/2015 | Reishus |
| D736,350 S | 8/2015 | Cheng |
| D736,887 S | 8/2015 | Schwarz |
| D747,441 S | 1/2016 | Naslund |
| D751,196 S | 3/2016 | Wapler |
| D753,823 S | 4/2016 | Hayamizu |
| D762,571 S | 8/2016 | Lee |
| D771,243 S | 11/2016 | DiMino |
| D798,686 S | 10/2017 | Barakat |
| D799,036 S | 10/2017 | Osada |
| D810,679 S | 2/2018 | Patton |
| D813,806 S | 3/2018 | Ito |
| D824,487 S | 7/2018 | Montoya |
| D824,488 S | 7/2018 | Montoya |
| D824,489 S | 7/2018 | Montoya |
| D824,490 S | 7/2018 | Montoya |
| D824,491 S | 7/2018 | Montoya |
| D824,626 S | 7/2018 | Vosbikian |
| D826,025 S | 8/2018 | Harrington |
| D831,212 S | 10/2018 | Clifford |
| D831,819 S | 10/2018 | Genender |
| D837,215 S | 1/2019 | Memke |
| D838,155 S | 1/2019 | Chen |
| D838,301 S | 1/2019 | Prikler |
| D840,032 S | 2/2019 | Clifford |
| D841,160 S | 2/2019 | Cranfield |
| D841,788 S | 2/2019 | Gough |
| D842,465 S | 3/2019 | Osada |
| D844,405 S | 4/2019 | Shen |
| D851,644 S | 6/2019 | Memke |
| D852,357 S | 6/2019 | Osada |
| D852,358 S | 6/2019 | Matuschek |
| D860,441 S | 9/2019 | Spycher |
| D864,857 S | 10/2019 | Clark |
| D865,289 S | 10/2019 | Huang |
| D869,927 S | 12/2019 | Waldron |
| D873,413 S | 1/2020 | Ohno |
| D873,957 S | 1/2020 | Daudish |
| D874,643 S | 2/2020 | Genender |
| D886,558 S | 6/2020 | Koenigsberger |
| D886,561 S | 6/2020 | Lundbaeck |

(56) References Cited

U.S. PATENT DOCUMENTS

| | | |
|---|---|---|
| D890,088 S | 7/2020 | Machida |
| D892,907 S | 8/2020 | Chan |
| D893,709 S | 8/2020 | Girod |
| D895,542 S | 9/2020 | Bell |
| D895,757 S | 9/2020 | Leis |
| D896,364 S | 9/2020 | Genender |
| D898,533 S | 10/2020 | Lundbaeck |
| D898,910 S | 10/2020 | Hansen |
| D900,737 S | 11/2020 | Hsu |
| D902,150 S | 11/2020 | Sun |
| D902,401 S | 11/2020 | Ohno |
| D904,608 S | 12/2020 | Attinger |
| D905,241 S | 12/2020 | Ohno |
| D905,520 S | 12/2020 | Huang |
| D906,076 S | 12/2020 | James |
| D907,456 S | 1/2021 | Diaz |
| D908,961 S | 1/2021 | Yang |
| D911,400 S | 2/2021 | Tsai |
| D918,088 S | 5/2021 | Fumex |
| 2002/0095068 A1 | 7/2002 | Bowski |
| 2003/0043042 A1* | 3/2003 | Moores, Jr. ............ G07C 11/00 340/573.1 |
| 2003/0146735 A1 | 8/2003 | Barbeau |
| 2004/0199052 A1 | 10/2004 | Banik |
| 2006/0041193 A1 | 2/2006 | Wright |
| 2006/0100483 A1 | 5/2006 | Sundet |
| 2006/0262525 A1 | 11/2006 | Barbeau |
| 2008/0041394 A1* | 2/2008 | Swann ................... A61B 17/42 128/831 |
| 2008/0086033 A1* | 4/2008 | Mihalca ................ A61B 1/123 600/160 |
| 2008/0139881 A1* | 6/2008 | Cover ................ A61B 1/00105 600/103 |
| 2008/0195128 A1 | 8/2008 | Orbay |
| 2009/0057544 A1 | 3/2009 | Brodie |
| 2010/0145146 A1 | 6/2010 | Melder |
| 2011/0092772 A1 | 4/2011 | Weber |
| 2011/0306834 A1 | 12/2011 | Schrader |
| 2011/0317403 A1 | 12/2011 | Fournier |
| 2013/0324794 A1 | 12/2013 | Covert et al. |
| 2013/0331730 A1 | 12/2013 | Fenech |
| 2014/0221749 A1 | 8/2014 | Grant |
| 2015/0366560 A1 | 12/2015 | Chen |
| 2017/0187212 A1 | 6/2017 | Hemesath |
| 2019/0142256 A1 | 5/2019 | Zhao et al. |
| 2019/0207402 A1* | 7/2019 | Ren ...................... H04R 25/602 |
| 2020/0205644 A1 | 7/2020 | Nakajima |

FOREIGN PATENT DOCUMENTS

| | | |
|---|---|---|
| KR | 300843231.0000 | 3/2016 |
| WO | WO 2018/048466 A1 | 3/2018 |

OTHER PUBLICATIONS

"Acupress Pen Stand Holder". Found online Dec. 29, 2020 at amazon.com. Reference dated Apr. 26, 2016. Retrieved from https://www.amazon.com/Acupress-Holder-Compatible-Intuos-CTL680/dp/B01ESYEWWU. (Year: 2016).

"Charging Dock and Base for Knuckle Lights Advanced". Found online Dec. 30, 2020 at knucklelights.com. Reference dated Jun. 25, 2019. Retrieved from https://knucklelights.com/products/charging-base. (Year: 2020).

"Kebor Hair Clippers". Found online Dec. 30, 2020 at amazon.com. Reference dated Apr. 19, 2019. Retrieved from https://us.amazon.com/Kebor-Clippers-Electric-Rechargeable-Lithium-ion/dp/B079GS6CDH. (Year: 2019).

"Revolabs Charger Base". Found online Dec. 30, 2020 at bhphotovideo.com. Reference dated Aug. 15, 2016. Retrieved from https://www.bhphotovideo.com/c/product/894848-REG/revolabs_02hddualchg11_charger_base_for_hd.html/qa. (Year: 2016).

"PULUZ Charging Dock". Found online Jan. 21, 2021 at miabyron.blogspot.com. Reference dated Jun. 3, 2019. Retrieved from https://miabyron.blogspot.com/2019/06/puluz-pu381-charging-dock-base-charger.html. (Year: 2018).

"Nikon Battery Charger Set". Found online Jan. 21, 2021 at newbecca.com. Reference dated Feb. 9, 2018. Retrieved from https://tineye.com/search/35fa9bc083a5e4b862a861548dc19c9785657fc7?sort=crawl_date&order=asc&page=1. (Year: 2018).

* cited by examiner

WIRELESS CAMERA SYSTEM FOR ENDOSCOPE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

Aspects of the present disclosure are directed to endoscopes, arthroscopes, and other medical imaging devices, and more particularly to a wireless camera system used with endoscopes, arthroscopes and other medical imaging devices, for example, in arthroscopic surgical procedures.

Description of the Related Art

Endoscopes and cameras are used in various surgical procedures, such as arthroscopic procedures. However, existing endoscopes and cameras are connected to cables to connect to power sources, which can become tangled during use and contribute to a crowded and disorganized operating room. Additionally, cables attached to the endoscope and/or camera can make it cumbersome for a user (e.g., surgeon) to reposition (e.g., rotate) the endoscope to provide a different view of the surgical area.

SUMMARY

In accordance with one aspect of the disclosure, a wireless camera for use in endoscopic procedures is provided.

In accordance with one aspect of the disclosure, a wireless camera for use with an endoscope or arthroscope is provided.

In accordance with another aspect of the disclosure, a wireless camera is provided that can removably couple to a battery-powered cordless endoscope.

In accordance with another aspect of the disclosure, a wireless camera is provided that can removably couple to a disposable battery-powered cordless endoscope.

In accordance with another aspect of the disclosure, a wireless camera is provided with a connector that can releasably couple to a cordless endoscope (e.g., to an eyepiece of the cordless endoscope) for use in a minimally invasive surgical procedure (e.g., an arthroscopic procedure).

In accordance with another aspect of the disclosure, a wireless camera is provided that removably couples to a cordless endoscope and wirelessly communicates with a controller (e.g., a controller box).

In accordance with another aspect of the disclosure, a wireless camera is provided that wirelessly communicates with a controller using radiofrequency (RF) communication.

In accordance with another aspect of the disclosure, a wireless camera is provided for use in endoscopic procedures that automatically pairs with a controller (e.g., a controller box).

In accordance with another aspect of the disclosure, a wireless camera system includes a wireless camera for use in endoscopic procedures (e.g., with a cordless endoscope) and that communicates wirelessly with a controller (e.g., controller box) using a protocol that inhibits (e.g., prevents) cross-talk with other wireless systems in an operating room, as well as interferences with other wireless devices.

In one implementation, the controller box is connected to a video monitor to display the images (e.g., photographs, video) communicated to the controller box by the wireless camera. The controller box has various data output options for data transmission of the images captured by the wireless camera and communicated to the controller box. For example, a USB drive, SD card, or other memory stick can be connected to a port of the controller box for outputting captured images from the controller box. The controller box can optionally output data (e.g., images captured by the wireless camera) to a remote electronic device (e.g., a tablet computer, laptop computer, smartphone, etc.). Optionally, the controller box can output data (e.g., images captured by the wireless camera) to a remote electronic device (e.g., a tablet computer, laptop computer, smartphone, etc.) in encrypted form, or using a security protocol (e.g., password protected images).

In accordance with another aspect of the disclosure a wireless camera system includes a wireless camera for use in endoscopic procedures (e.g., with a cordless endoscope) and that communicates wirelessly with a controller (e.g., controller box) using a protocol that inhibits (e.g., prevents) cross-talk with other wireless systems in an operating room, while the wireless camera is at least 15 feet away (e.g., 15 feet, 17 fee, 20 feet) from the controller (e.g., controller box).

In accordance with another aspect of the disclosure, a wireless camera for use in endoscopic procedures (e.g., used with a cordless endoscope) is provided, where the wireless camera has a rechargeable battery. In one implementation, the rechargeable battery is in or part of a detachable module of the wireless camera.

In accordance with another aspect of the disclosure, a wireless camera for use in endoscopic procedures (e.g., used with a cordless endoscope) is provided, where the wireless camera is autoclavable. In one implementation, the wireless camera that is autoclavable can be used with an endoscope that is not autoclavable.

In accordance with another aspect of the disclosure, a wireless camera for use in endoscopic procedures (e.g., used with a cordless endoscope) is provided, where the wireless camera has an ergonomic housing with control inputs on the housing actuatable by a user. In one implementation, such control inputs are actuatable by a user to select a photographic snapshot or a video recording with the camera.

DETAILED DESCRIPTION

Figure 1:
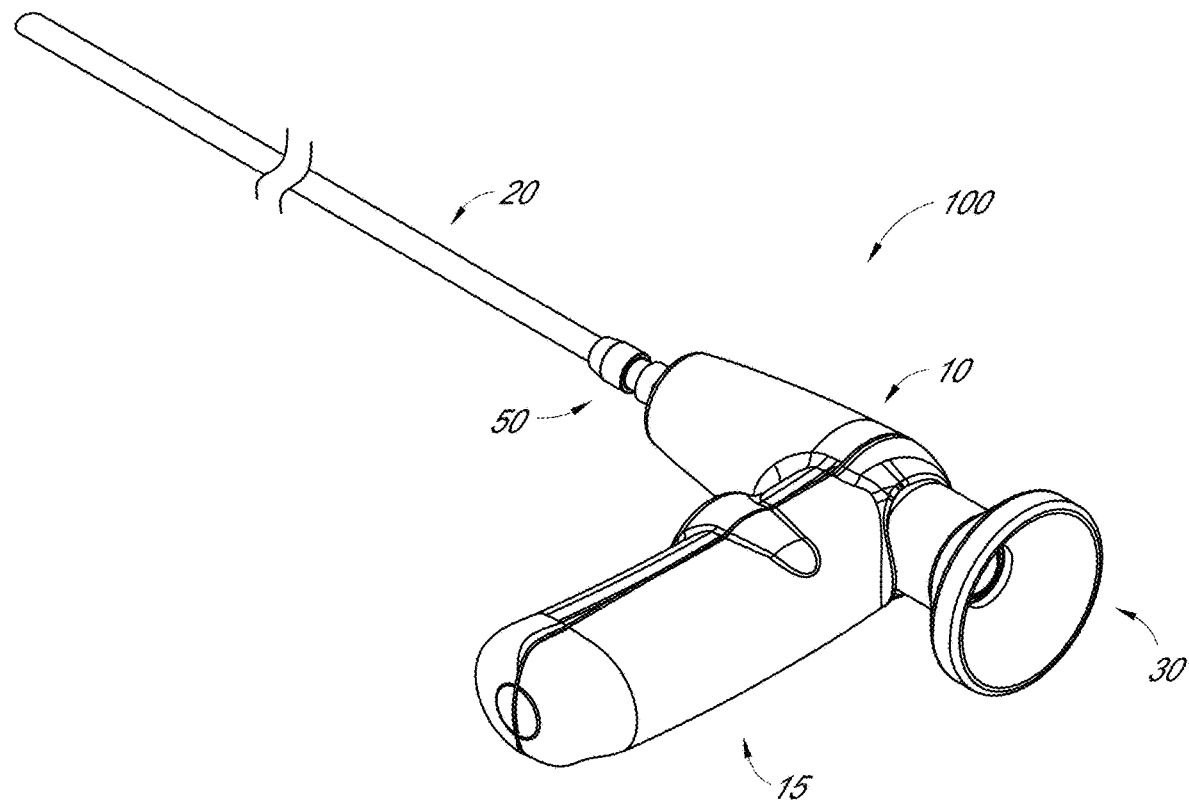
FIG. 1 is a perspective view of an endoscope (e.g., an arthroscope).
Figure 2:
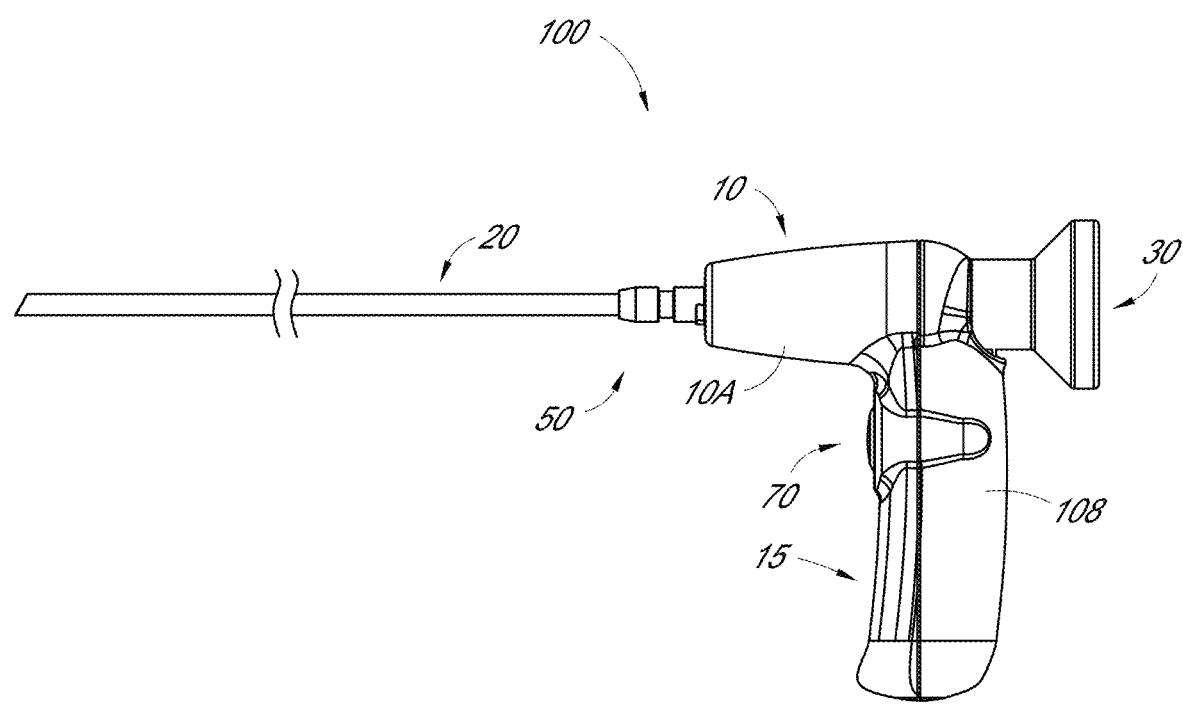
FIG. 2 is a side view of the endoscope of FIG. 1.

Disclosed herein is a wireless camera system for use in endoscopic procedures, such as with an endoscope (e.g., a cordless endoscope) for viewing inside a cavity of a body or through an incision in tissue. For illustrative purposes, FIGS. 1-2 illustrates an endoscope 100 such as, for example, an arthroscope, that can be used to inspect one or more portions of a human body. For example, in one implementation, the endoscope 100 can be employed to inspect the interior of a knee (e.g., during an arthroscopic procedure on the knee).

The endoscope 100 (e.g., arthroscope) can have a housing 10, an endoscope tube or elongate member 20 (e.g., a rigid endoscope tube), and an eyepiece (e.g., eyecup, eyeshield) 30. The handle 15 of the endoscope 100 can extend orthogonal (e.g., perpendicular to the axis of the endoscope tube 20). The endoscope tube or elongate member 20 can optionally be made of stainless steel. In some implementations, the endoscope 100 can advantageously be disposable (e.g., single use).

The endoscope tube or elongate member 20 can have one or more (e.g., a plurality) of lenses disposed within an elongate tubular structure having proximal and distal ends. In some implementations, the lenses can be made of glass. In other implementations, the lenses can be made of plastic, such as polymethyl methacrylate (PMMA), Cyclic olefin copolymer (COC), or Cyclic olefin polymer (COP). The lenses can relay an image of features in the body located at the distal end of the endoscope 100 to the proximal end of the endoscope 100. In some embodiments, an imaging device (e.g., a camera or a detector such as a two-dimensional CCD or CMOS detector array) can be attached to the proximal end of the endoscope 100 to sense the relayed image. In some implementations, the eyepiece 30 or other optics may be used to view the image. In certain implementations, the endoscope 100 may additionally have a light source that is configured, sized, and positioned so as to be inserted into the body cavity to provide illumination therein. In some embodiments, for example, this light source is disposed at the distal end of the endoscope tube or elongate member 20. In some implementations, this light source comprises at least one solid state emitter, such as a light emitting diode (LED), located at the distal end of the endoscope.

In operation, light emitted from the light source illuminates various objects, surfaces, and features (e.g., walls) in the interior of the body cavity and is reflected off objects, surfaces, and features (e.g., walls) in the interior of the body cavity. A portion of the reflected light may be collected through an aperture at the distal end of the elongate member 20. This light may be directed along an optical path through the elongate member 20 formed by the plurality of lenses disposed in the elongate tubular structure so as to form an image of the objects, surfaces, features at the proximal end of the endoscope 100. The light collected may then be directed to the imaging device. Thus, an image of the object, surface, feature, etc. inside the body cavity can be viewed, for example, by the physician possibly on a display in communication with the detector.

Figure 3A:
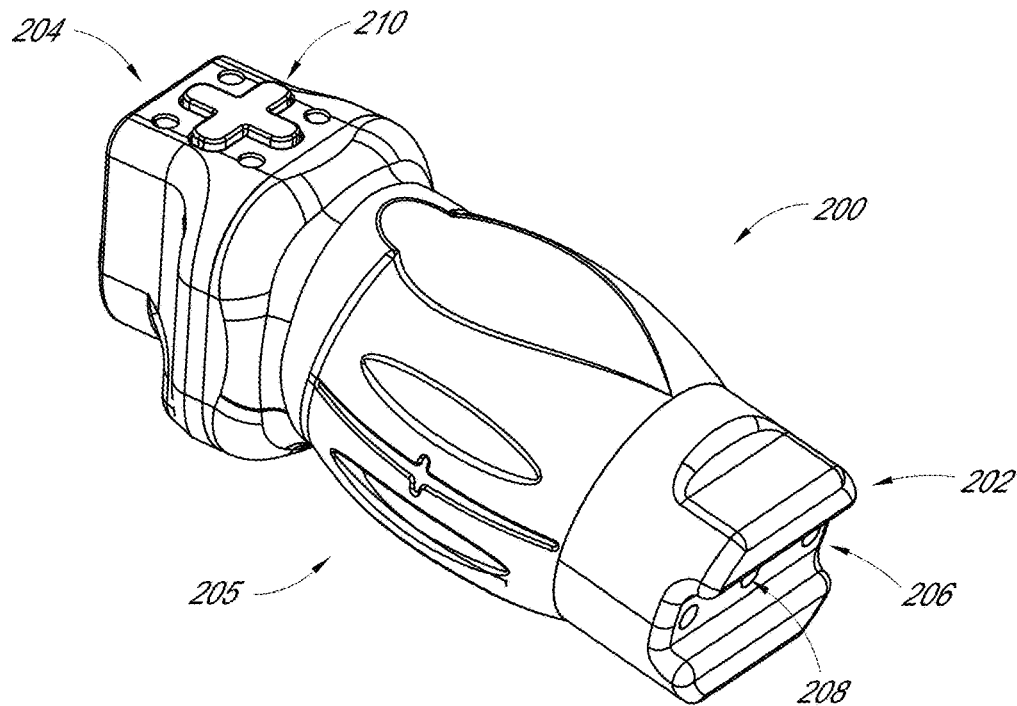
FIG. 3A is a perspective view of one embodiment of a wireless camera for use with the endoscope of FIG. 1.

FIG. 3A shows a wireless camera 200 with an ergonomic body 205 that extends from a proximal end 202 to a distal end 204. At least a portion of the ergonomic body 205 can be made of a resilient material (e.g., plastic, rubber, a polymer material) and has one or more grip features thereon. At least a portion of the ergonomic body 205 is curved (e.g., bulbous) and can be held in a palm of a user's hand (e.g. user's hand can be wrapped around at least a portion of the ergonomic body 205). The ergonomic body 205 allows the user (e.g., surgeon to easily hold the camera for extended periods of time (e.g., during a surgical procedure) and to easily reposition the camera 200 in space. The wireless camera 200 has one or more rechargeable batteries (e.g., Alkaline, Lithium ion) in a power or battery module 206. the power or battery module 206 has one or more electrical contacts 208 via which the batteries can be charged. The wireless camera 200 also has on or more control inputs 210 (e.g., one or more buttons, multiple buttons, cross-shaped input) via which the operation of the camera 200 can be controlled by a user (e.g., to power the camera on/off, to select video recording by the camera, to select photo snapshots by the camera, to automatically zoom-in on image).

Figure 3B:
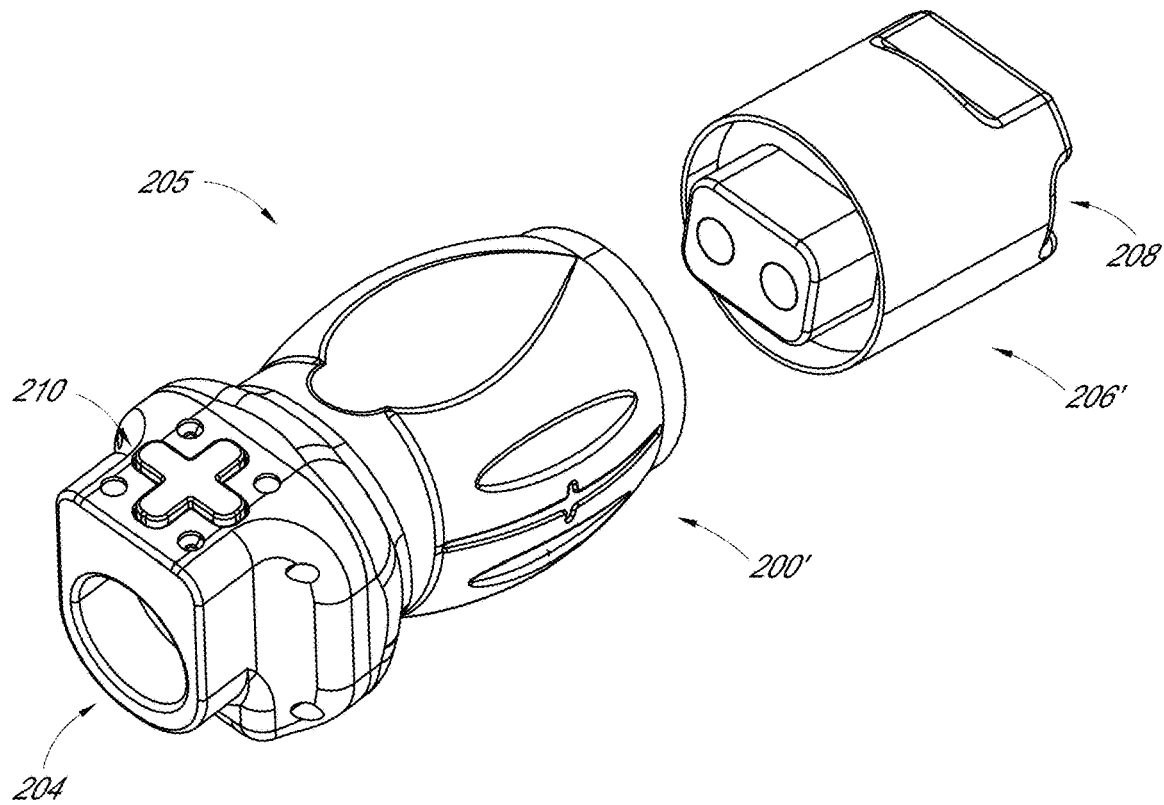
FIG. 3B is a perspective exploded view of another embodiment of a wireless camera for use with the endoscope of FIG. 1.

FIG. 3B shows a wireless camera 200'. The features of the wireless camera 200' are similar to features of the wireless camera 200 in FIG. 3A. Thus, references numerals used to designate the various components of the wireless camera 200' are identical to those used for identifying the corresponding components of the wireless camera 200 in FIG. 3A, except that an "'" has been added to the numerical identifier. Therefore, the structure and description for the various features of the wireless camera 200 in FIG. 3A are understood to also apply to the corresponding features of the wireless camera 200' in FIG. 3B, except as described below.

The wireless camera 200' differs from the wireless camera 200 in that the power or battery module 206' is detachable. Therefore, the wireless camera 200' allows for the same battery module 206' to be used in multiple cameras 200'. Also, the power or battery module 206' can be detached from the ergonomic body 305 and coupled to a charging base, as described below, without having to place the assembled wireless camera 200' (e.g., ergonomic body 205 attached to the battery module 206') on the charging base.

Figure 3C:
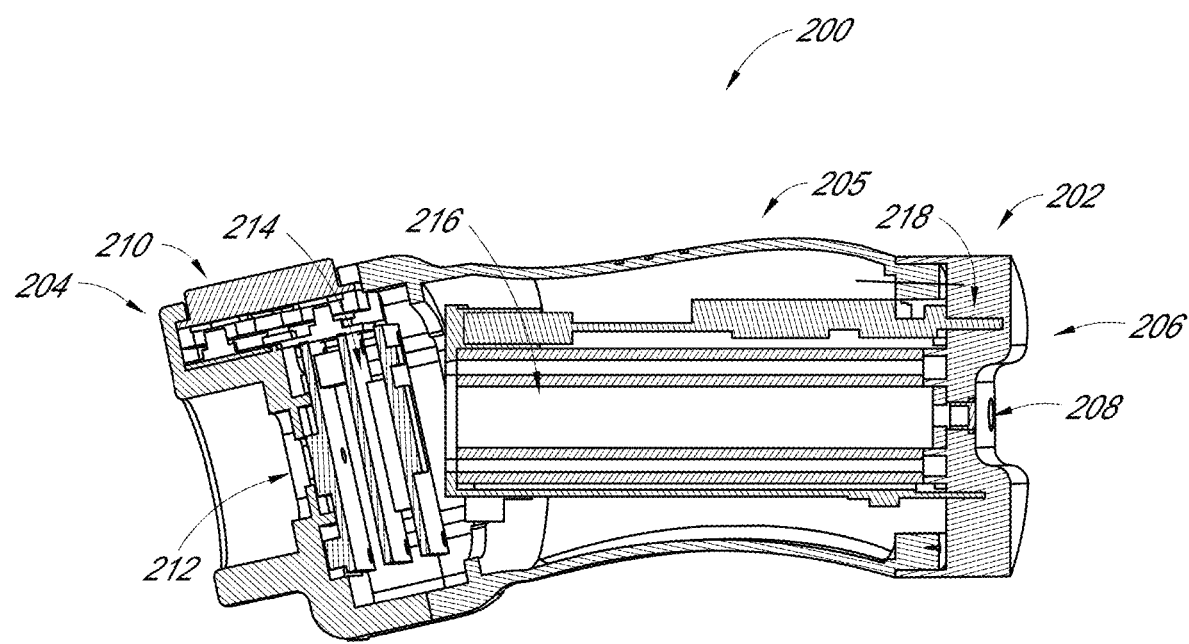
FIG. 3C is a cross-sectional side view of the wireless camera of FIG. 3A.

FIG. 3C shows a cross-sectional side view of the wireless camera 200. The camera 200 includes a sensor (e.g., an image sensor) 212 proximate the distal end 204 of the camera 200, circuitry (e.g., in or on one or more printed circuit board assemblies PCBAs) 214, one or more batteries (e.g., alkaline, Lithium ion, AA size, AAA size) 216, and one or more antennas (e.g., two antennas) 218 proximate the proximal end 202 of the camera 200. The antenna(s) 218 in one implementation are directed toward the proximal end 202 of the camera 200 (e.g., facing out of the back or proximal end 202 of the camera 200). The antenna(s) 218 can be wholly enclosed (e.g., housed) in the camera 200 (e.g., in the body 205) and not protrude or otherwise extend from a surface of the body 205 or battery module 206.

Figure 4:
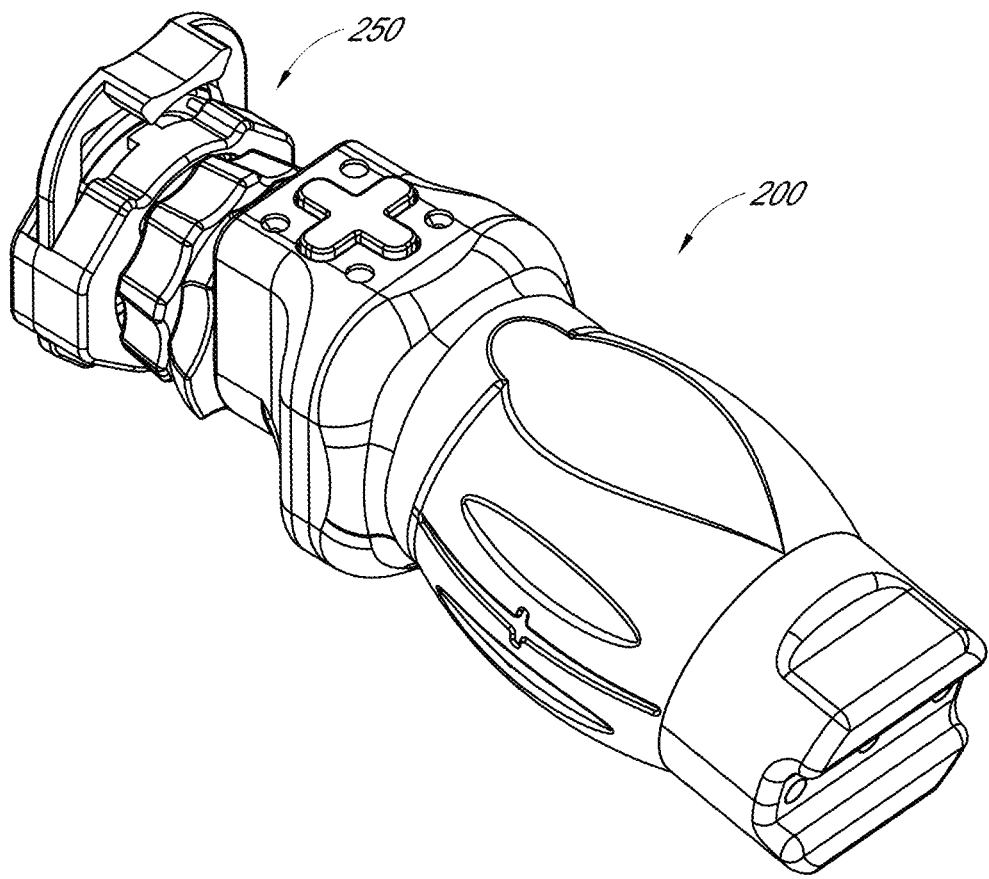
FIG. 4 is a perspective view of the wireless camera of FIG. 3A with a connector.
Figure 5:
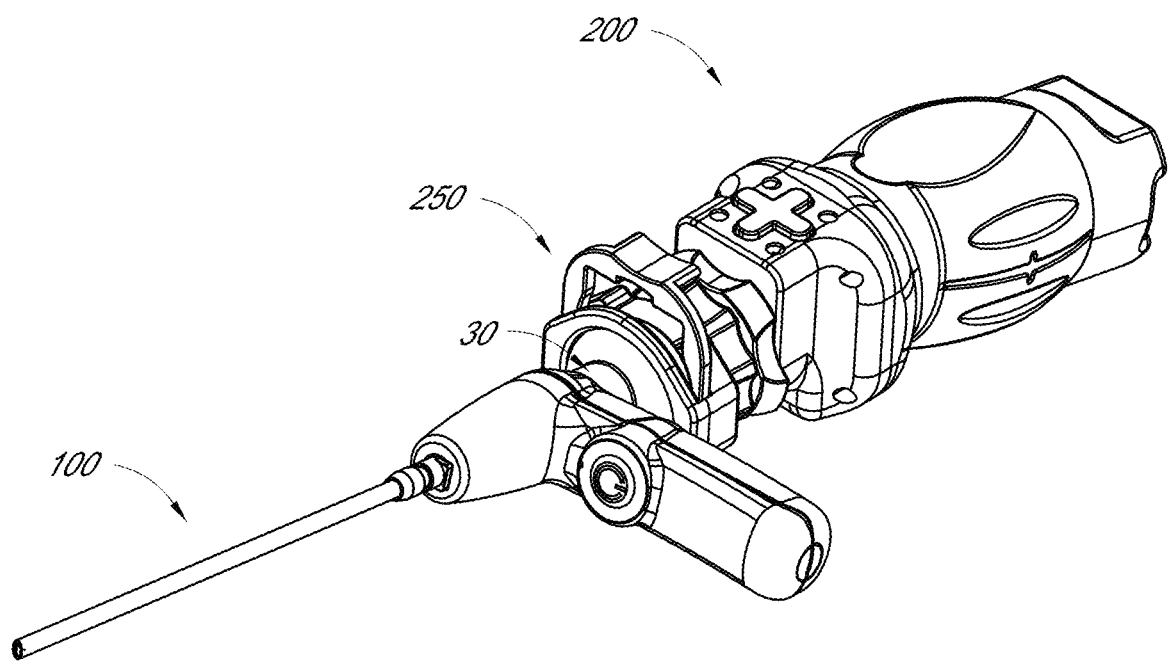
FIG. 5 is a perspective view of the wireless camera with the connector of FIG. 4 coupled to the endoscope of FIG. 1.

With reference to FIGS. 4-5, a connector 250 can be coupled to the distal end 204 of the wireless camera 200, 200', and the connector 250 can releasably couple to the cordless endoscope 100 (e.g., clamp to an edge or surface of the eyepiece 30 of the endoscope 100) to fixedly couple the wireless camera 200, 200' to the cordless endoscope 100. The camera 200 can extend generally linearly (e.g., along the same axis, along a substantially parallel axis) with the endoscope tube 20 when the wireless camera 200 is coupled to the endoscope 100. Advantageously, the coupled wireless camera 200 and cordless endoscope 100 allows a user (e.g., surgeon) to easily and readily reposition the orientation of the endoscope 100 and camera 200 (e.g., rotate the camera 200 along with the endoscope 100 to gain a different viewpoint of the surgical site). Additionally, since the endoscope 100 and camera 200 are both cordless or wireless, the assembly advantageously facilitates the decluttering of the operating room (e.g., by avoiding additional cables for these devices, and the possible entanglement or inadvertent disconnection of such cables).

The wireless camera 200, 200' for use in endoscopic procedures (e.g., used with a cordless endoscope) is autoclavable. In one implementation, the wireless camera 200, 200' that is autoclavable can be used with an endoscope 100 that is not autoclavable.

Figure 6A:
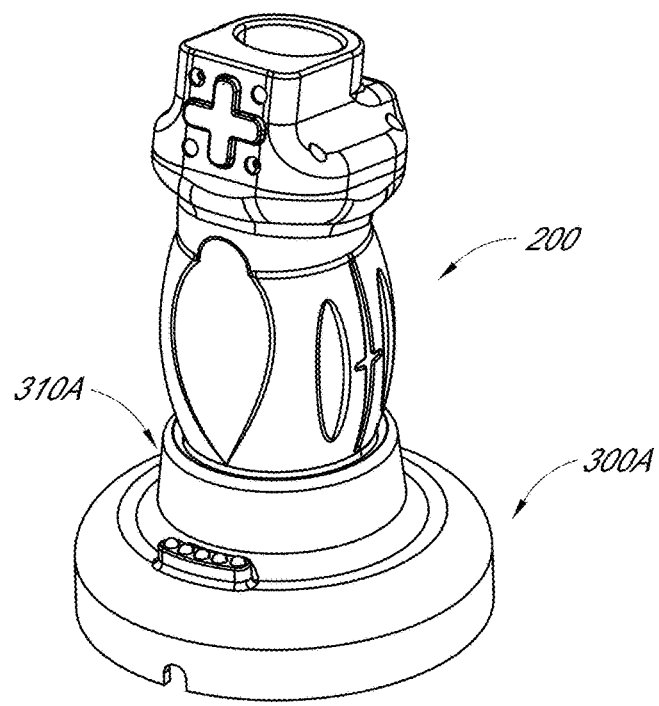
FIG. 6A is a perspective view of the camera of FIG. 3A on a single dock charging base.
Figure 6B:
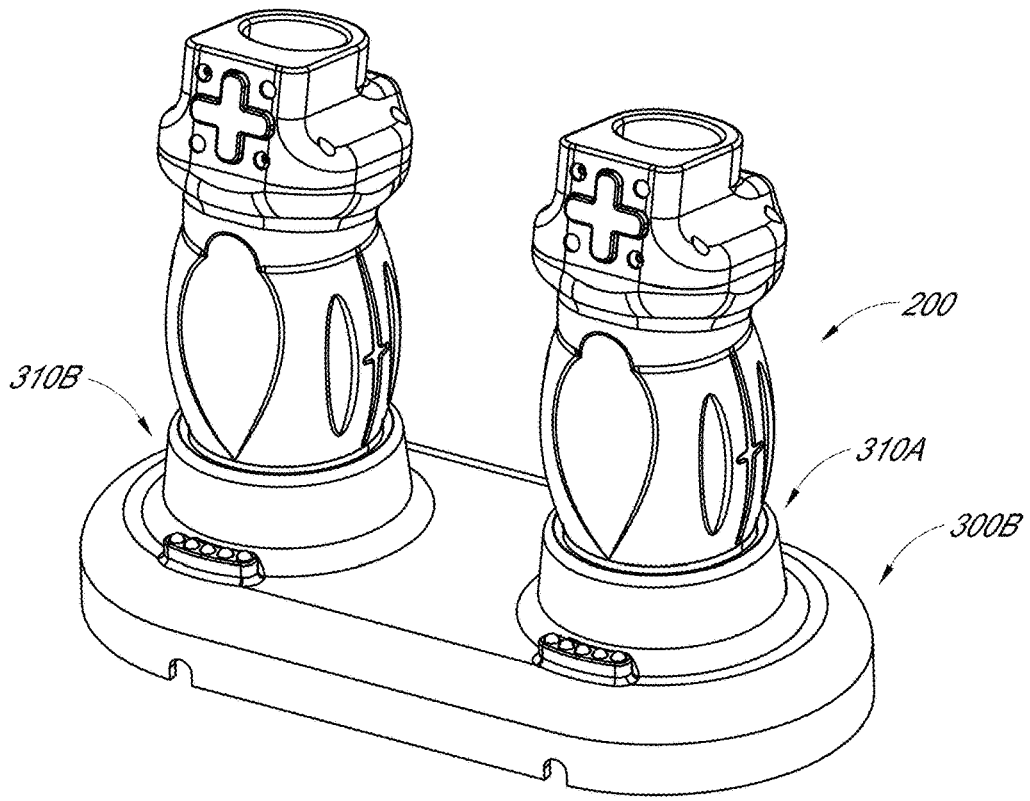
FIG. 6B is a perspective view of a pair of the cameras of FIG. 3A in a dual dock charging base.

With reference to FIGS. 6A-6B, charging units can be used to charge the wireless camera 200, 200'. FIG. 6A shows a charging unit 300A with a single dock 300A for receiving a single camera 200, 200' for charging of its batteries (e.g., in the battery module 206, 206'). FIG. 6B shows a charging unit 300B having two docks 310A, 310B for receiving a pair of cameras 200, 200' for charging of their batteries (e.g., in the battery module 206, 206'). Also, the charging base 300A, 300B can have one or more (e.g., multiple, two or more) docks 310A, 310B.

Figure 7:
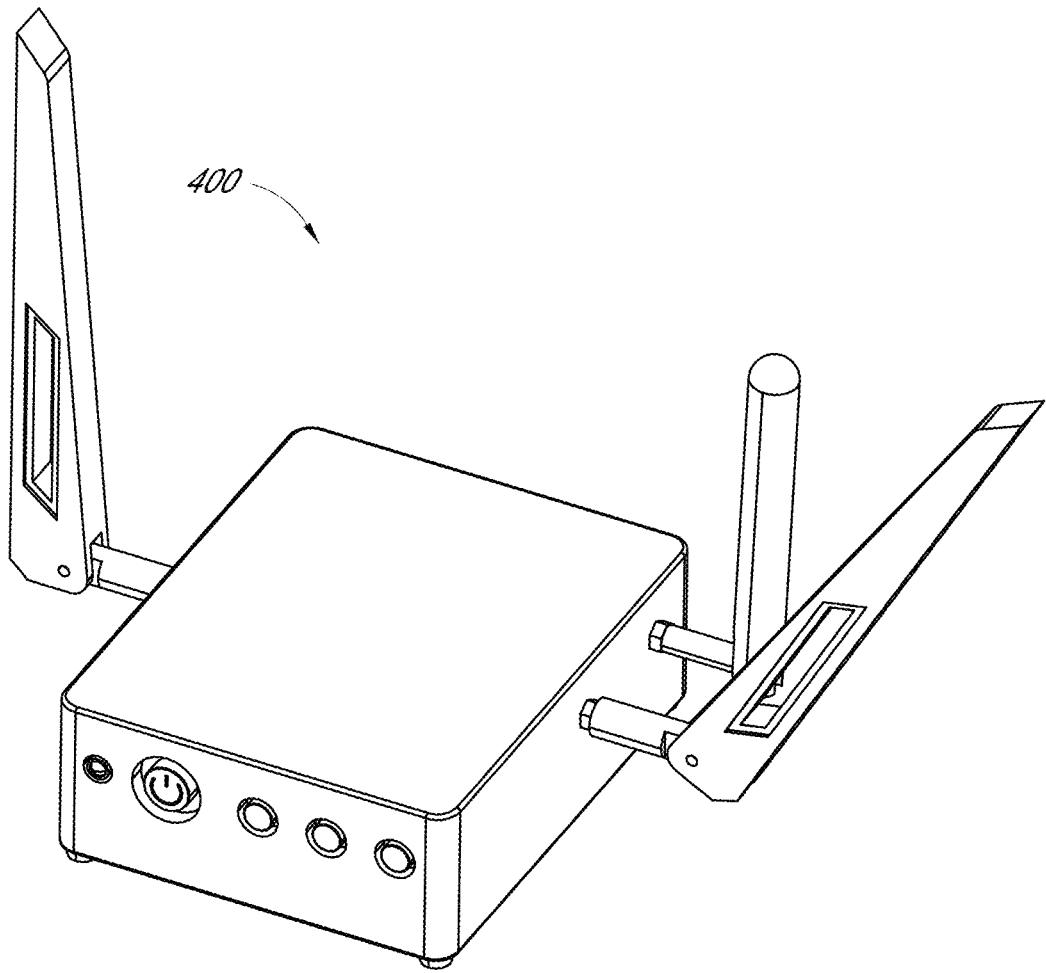
FIG. 7 is a perspective view of a controller for use with the wireless camera of FIGS. 3A-3B.

FIG. 7 shows a controller or controller box 400 that can wireless communicate (e.g. via radiofrequency or Rf communication) with the wireless camera 200, 200' to receive data (e.g., still images, video) captured by the wireless camera 200, 200'. The controller 400 can be located remotely from the wireless camera 200, 200'. For example, the controller 400 can be located 15 feet or less from, approximately 15 fee from, or between 15-25 feet from the wireless camera 200, 200'.

Figure 8:
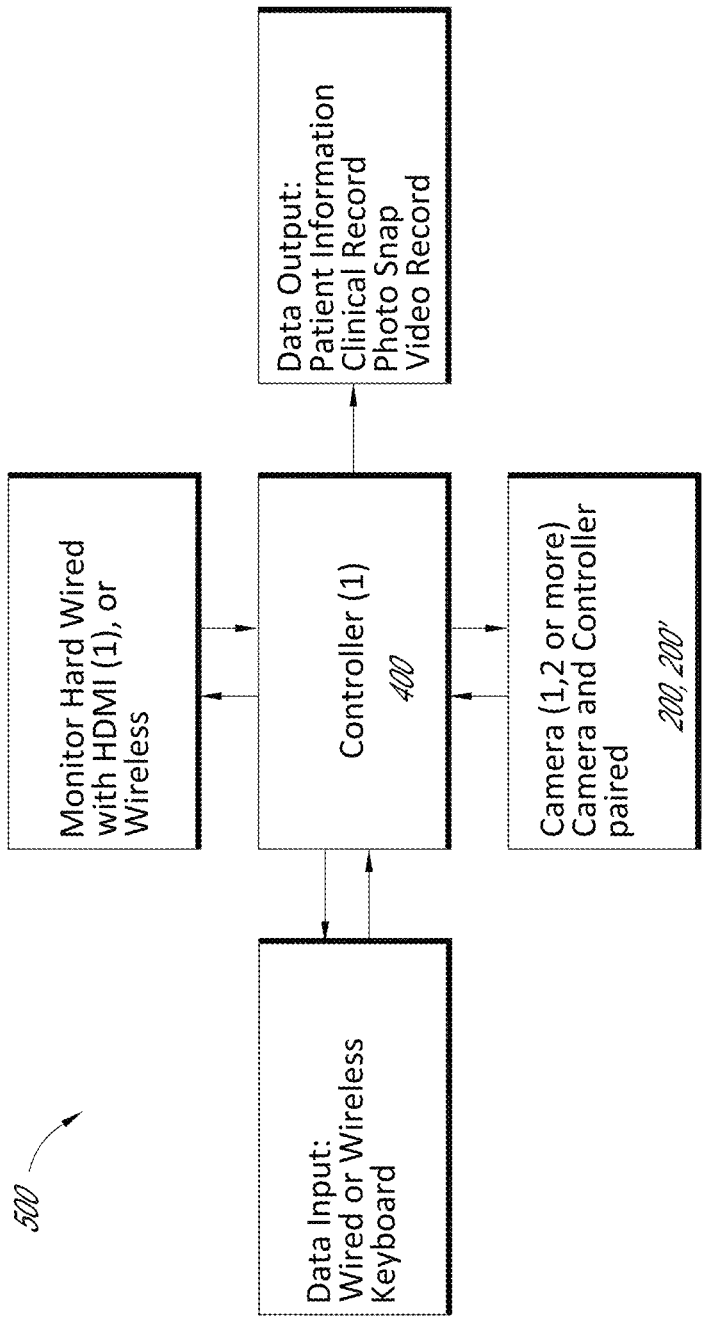
FIG. 8 is a schematic view of a wireless camera system.

FIG. 8 shows a schematic of a wireless camera system 500. The system 500 includes a controller, such as the controller box 400. The controller communicates (e.g., via two-way communication) with one or more wireless cameras, such as the wireless cameras 200, 200'. The controller also communicates (e.g., wirelessly or via a wired connection), via two-way communication, with an electronic display, such as an image or video monitor, television, etc. The controller also communicates (e.g., via two-way communication) with a data input module (e.g., a wired or wireless keyboard), and communicates (e.g., via one-way communication) with a data output module or port to output data (e.g., snapshots or video recordings captured by the camera 200, 200', patient information, clinical record, etc.). Therefore, the controller (e.g., the controller box 400) can output data to both the monitor and the data output module or port (e.g., simultaneously).

Figure 9:
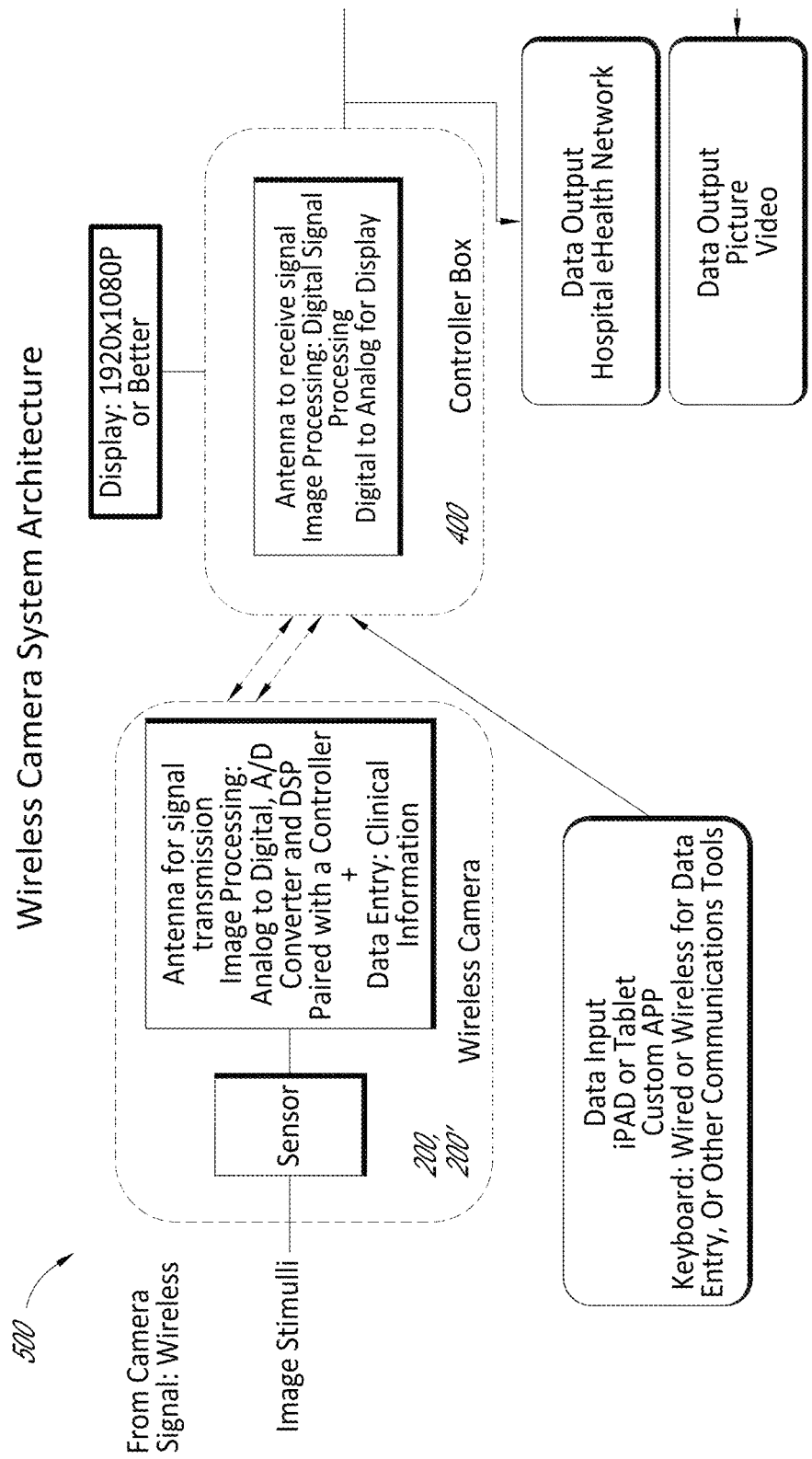
FIG. 9 is a schematic of a wireless camera system architecture.

FIG. 9 shows a more detailed schematic view of the wireless camera system 500. The controller, such as the controller box 400, can include one or more antennas to receive data (e.g., digital signals) from one or more wireless cameras, such as wireless camera 200, 200'. The controller can include image processing circuitry, such as for processing the digital signals received from the camera 200, 200'. The controller can also include circuitry for converting digital signals to analog signals for transmission to the electronic display (e.g., monitor, television). Optionally, the electronic display can display images in high definition (e.g., 1920×1080P resolution or better, such as 4K). As discussed above, the controller (e.g., controller box 400) can additionally or alternatively output data (e.g., images, recorded video) to an output location (e.g., a remote computer or computer network, such as in a hospital).

With continued reference to FIG. 9, the wireless camera, such as the wireless camera 200, 200', includes one or more antennas (e.g., 218 in FIG. 3C) to transmit data (e.g., digital signals for still or snapshot images and/or video recordings) to the controller (e.g. to the controller box 400). The wireless camera 200, 200' can have circuitry that communicates with the one or more antennas and one or more sensors that receives one or more images (e.g., snapshots, video recordings) from an endoscope (e.g. the cordless endoscope 100) coupled to the wireless camera 200, 200'. In one implementation, the sensor can be a 35 mm equivalent sensor for wide angle views. The circuitry can include one or more modules for transmitting signals (e.g., digital signals) to the controller (e.g., controller box 400), image processing modules, such as for converting analog to digital signals, an analog to digital converter, a digital signal processor or DSP, and circuitry for pairing the camera 200, 200' with the controller (e.g., controller box 400). As discussed above, the controller (e.g., controller box 400) can receive data input (e.g., via a wired or wireless connection) from one or more sources (e.g., a keyboard, remote electronic device such as a tablet computer).

The antennas 218 (see FIG. 3C) in the camera 200, 200' and the controller box 400 are positioned to be able to communicate without any loss of transmission of data.

Figure 10:
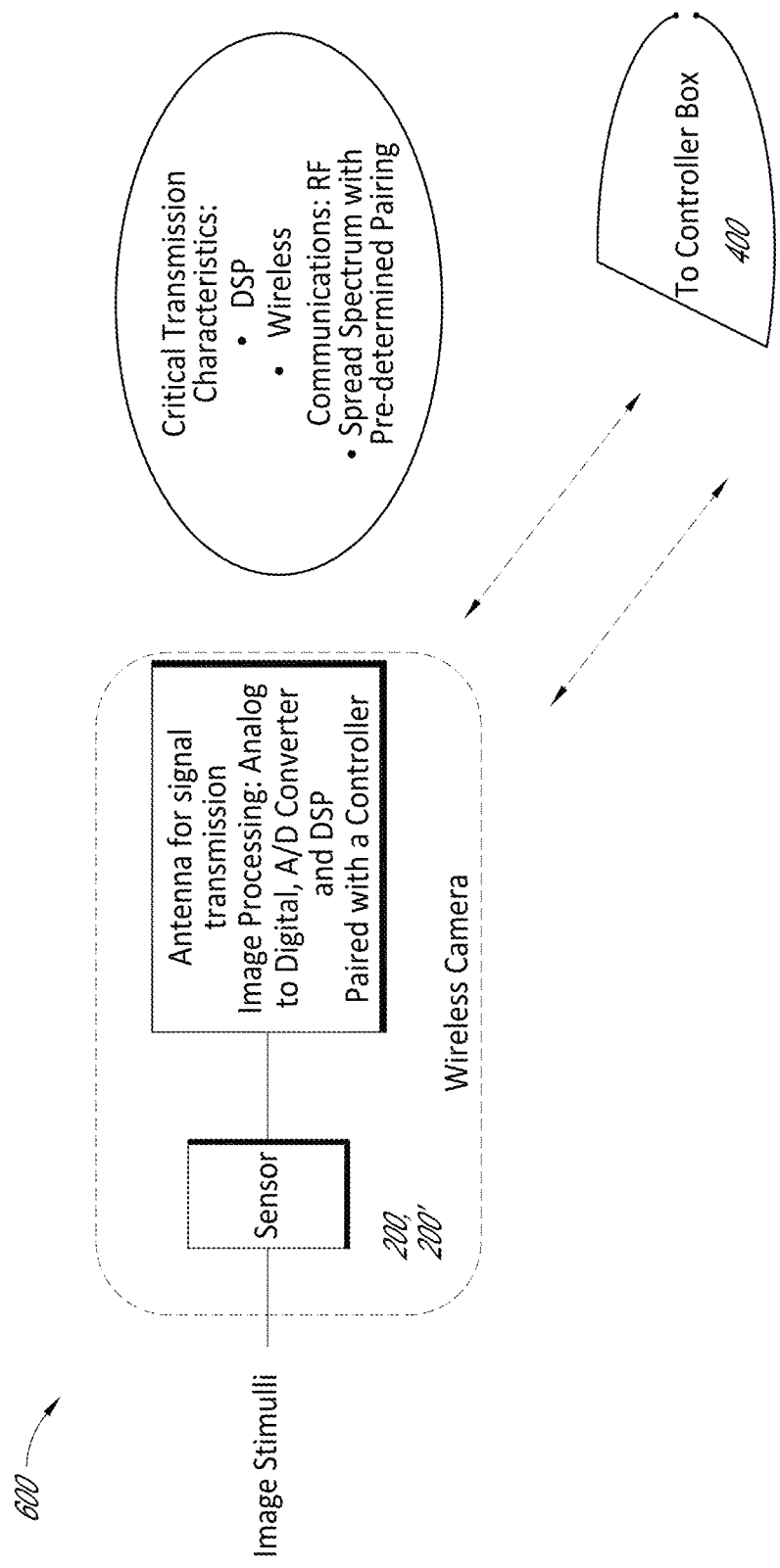
FIG. 10 is a schematic diagram of signal processing for wireless transmission in a wireless camera.
Figure 11:
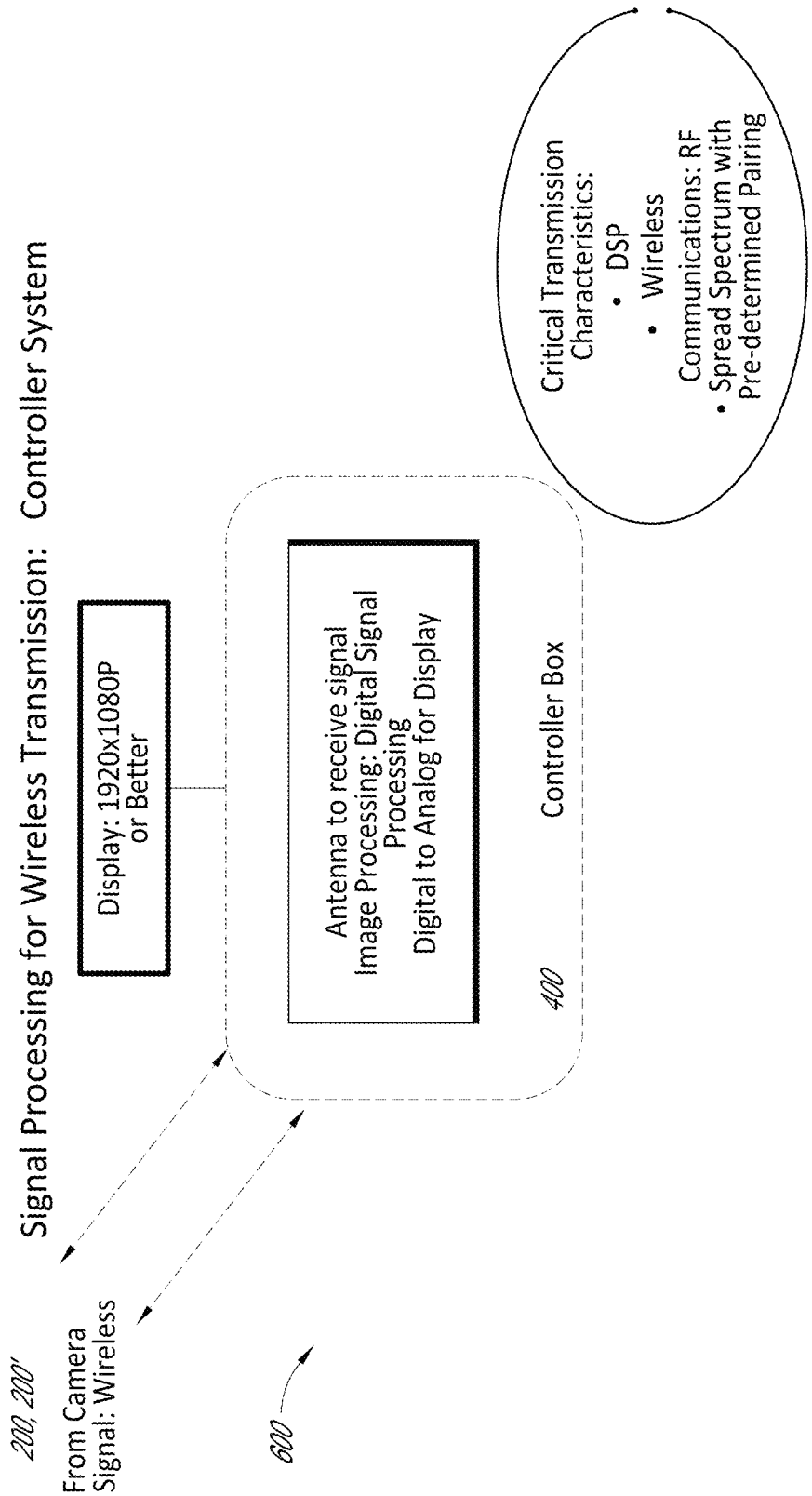
FIG. 11 is a schematic diagram of signal processing for a controller box for use with the wireless camera of FIGS. 3A-3B.

FIG. 10 shows a schematic view of a portion of a signal processing diagram for wireless transmission of data from a camera, such as the camera 200, 200', to a controller, such as the controller 400, showing communications transmitted from the camera. FIG. 11 shows another portion of the signal processing diagram for wireless transmission of data from a camera, such as the camera 200, 200', to a controller, such as the controller 400, showing communications received by the controller. The controller (e.g., controller box 400) can be paired with one or more cameras (e.g., camera 200, 200'). Optionally, only one operating camera at a time can be paired with the controller 400.

The wireless camera 200, 200' can communicate wirelessly with the controller (e.g., controller box 400). The wireless communication frequency can be within the radiofrequency modality, such as frequencies in the RF band, such as in or near 2.0-8.0 GHz (e.g., 2.4 GHz, 5.0 GHz) frequency band. Data transmission from the wireless camera 200, 200' to the controller box 400 can be through wideband communication and utilize spread spectrum frequency transmission. Advantageously, instead of using frequency hopping for data transmission, the wireless camera system 500 utilizes an Orthogonal Frequency Division Multiplexing (OFMD) or a Direct Sequence (DS) protocols. OFMD enables the communications of the controller box 400 with the camera 200, 200' without interference from other systems in the operating room, such as microwave or RF (radiofrequency) ablation devices. The use of OFMD advantageously provides the wireless camera system 500 with resistance to interference, cross-communications between different devices, resistance to interception (of transmitted data), and resistance to fading that causes blurry images.

Spread Spectrum is a communications method where a transmitting signal is spread over a bandwidth in excess of the minimum bandwidth necessary to send the signal. Signal spreading is done before sending the signal. The same signal is used at the receiver end (e.g., the controller or controller box 400) as in the transmitter end (e.g., in the camera 200, 200'). Thus, the signal is a peer to peer signal. Therefore, the signal can be pre-defined with specific coding such that it will be resistant to any external jamming and interception. Spread Spectrum provides increased security, encryption and authentication for the wireless communication between the camera 200, 200' and the controller (e.g., controller box 400).

The camera 200, 200' communicates with the controller (e.g., controller box 400) with a peer-to-peer communication via use of spread spectrum design of modified DSSS (Direct Sequence Spread Spectrum) (FDMA). This communications protocol requires that the camera 200, 200' and the controller box 400 are paired. A plurality (e.g., two to eight) cameras 200, 200' can optionally be paired with one controller (e.g., controller box 400); however, in one implementation only one camera 200, 200' is in use at a given time. The camera 200, 200' and the controller (e.g., controller box 400) have a secure connection that inhibits (e.g. prevents) cross-talk with other nearby electronic (e.g., wireless) devices (e.g., infusion pumps or other medical equipment in the operating room).

During use, the signal for each paired camera system 500 (e.g., each paired camera 200, 200' and controller box 400) is using an FHSS (Frequency Hopping Spread Spectrum) or DSSS (Direct Sequence Spread Spectrum) communication algorithm. In case of FHSS, the camera signal is frequency hopping according to a unique predetermined sequence. In DSSS, the data signal is multiplied by spreading code and resulting signal occupies a much higher frequency band. The spreading code is a pseudo-random sequence. This signal processing technique used by the camera system 500 (e.g., paired camera 200, 200' and controller box 400) is unique and employs the spread spectrum communication methodology, including encryption and modified DSSS or FHSS algorithms.

The wireless camera system 500 also utilizes frequency divisional multiple access (FDMA). FDMA allocates specific carrier frequency to a communication channel. The number of different cameras is limited to the number of "slices" in the frequency spectrum. Methods of FDMA access include radio broadcasting, TV, AMPS, and TETRA-POLE. The wireless camera system 500 combines the use of FDMA and Code Division Multiple Access (CDMA) for a controlled and efficient communication of data that prevents interference and noise during signal transmission.

Figure 12:
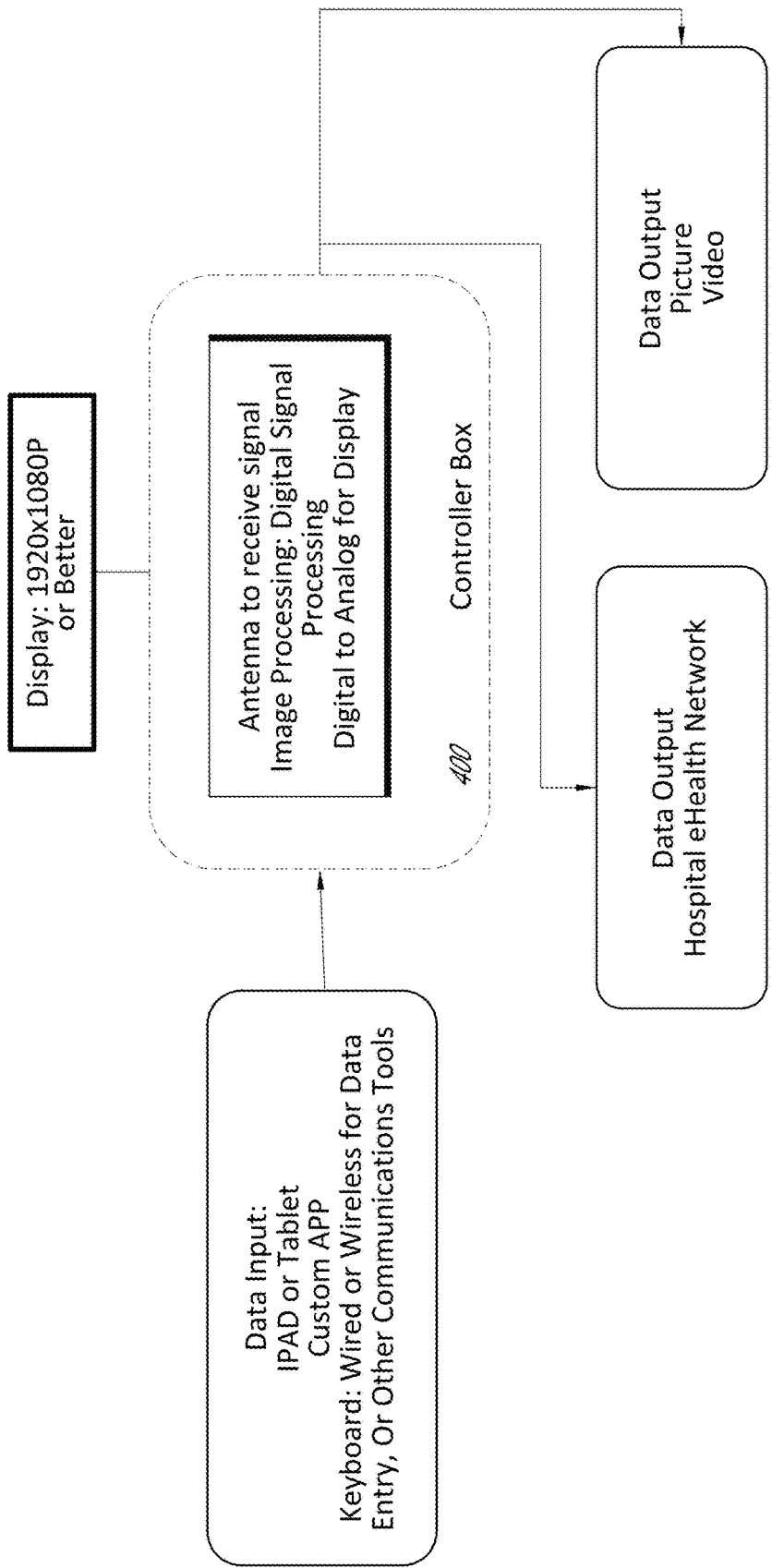
FIG. 12 is a schematic diagram of data input and output in a wireless camera system.

FIG. 12 shows a data input and data output diagram for the wireless camera system 500. The controller, such as the controller box 400, can receive input from the one or more sources (e.g., in a wired or wireless manner), such as from a tablet computer, or keyboard, laptop, etc. The controller, such as the controller box 400, can output data to an electronic display (e.g., a monitor or television with high definition, such as 1920×1080P or better resolution, such as 4K). The controller can also output data to an output module for use by a clinician (e.g., to a USB drive or other portable memory stick, to a remote computer or computer network, hard disk, compact flash drive, email, etc.).

While certain embodiments of the invention have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the devices described herein need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed devices.

What is claimed is:

1. A wireless endoscopy system, comprising:
a wireless camera comprising an ergonomic body and a rechargeable battery, the ergonomic body including a bulbous portion with a width that is largest at an intermediate location between a proximal end and a distal end of the ergonomic body, the ergonomic body configured to contact a palm of a user's hand that is wrapped around the bulbous portion;
a connector configured to attach to a distal end of the wireless camera; and
a cordless endoscope having an eyepiece, an ergonomic handle sized to be held between a palm and one or more fingers of a user's hand, and an endoscope tube that extends distally of the handle,
wherein the wireless camera releasably couples to the eyepiece of the endoscope via the connector, the wireless camera operable to capture and wirelessly transmit one or both of an image signal and a video signal, and
wherein the wireless camera is autoclavable and is operable to capture and wirelessly transmit one or both of an image signal and a video signal in one or both of a direct sequence spread spectrum algorithm and a frequency hopping spread spectrum algorithm.

2. The system of claim 1, wherein the wireless camera has one or more electrical contacts via which the rechargeable battery is recharged.

3. The system of claim 1, further comprising a charging base having one or more docks configured to receive at least a portion of the camera to recharge the rechargeable battery.

4. The system of claim 1, wherein the wireless camera has a detachable battery unit that houses the rechargeable battery, the detachable battery unit configured to releasably couple to the ergonomic housing.

5. The system of claim 1, wherein the wireless camera comprises a cross-shaped user input actuatable by a user to control an operation of the wireless camera.

6. The system of claim 1, wherein the wireless camera comprises one or more antennas in a proximal portion of the wireless camera.

7. The system of claim 1, wherein the wireless camera and the cordless endoscope are rotatable as a single unit when the wireless camera is coupled to the cordless endoscope.

8. The system of claim 1, wherein the wireless camera and the cordless endoscope are rotatable as a single unit about an axis of the endoscope tube when the wireless camera is coupled to the cordless endoscope.

9. The system of claim 1, wherein the connector encloses at least a portion of the eyepiece when the wireless camera couples to the cordless endoscope.

10. The system of claim 1, wherein the ergonomic body has a convex surface configured to receive at least a portion of a user's hand thereon.

11. The system of claim 1, wherein the ergonomic body comprises one or more grip features configured to contact at least a portion of a user's hand to facilitate gripping of the wireless camera by the user.

12. The system of claim 1, wherein the endoscope handle extends orthogonal to the endoscope tube.

13. A wireless endoscopy system, comprising:
a wireless camera comprising an ergonomic body and a rechargeable battery, the ergonomic body including a bulbous portion with a width that is largest at an intermediate location between a proximal end and a distal end of the ergonomic body, the ergonomic body configured to contact a palm of a user's hand that is wrapped around the bulbous portion; and a connector at a distal end of the wireless camera, wherein the wireless camera is configured to releasably couple to a cordless endoscope via the connector, the wireless camera operable to capture and wirelessly transmit one or both of an image signal and a video signal, and wherein the wireless camera is autoclavable and is operable to capture and wirelessly transmit one or both of an image signal and a video signal in one or both of a direct sequence spread spectrum algorithm and a frequency hopping spread spectrum algorithm.

14. The system of claim 13, wherein the wireless camera has one or more electrical contacts via which the rechargeable battery is recharged.

15. The system of claim 13, wherein the wireless camera has a detachable battery unit that houses the rechargeable battery, the detachable battery unit configured to releasably couple to the ergonomic housing.

16. The system of claim 13, wherein the wireless camera comprises a cross-shaped user input actuatable by a user to control an operation of the wireless camera.

17. The system of claim 13, further comprising a cordless endoscope having an ergonomic handle sized to be held between a palm and one or more fingers of a user's hand, the wireless camera coupleable to the endoscope via the connector.

18. The system of claim 13, wherein the connector encloses at least a proximal portion of the cordless endoscope when the wireless camera couples to the cordless endoscope.

19. The system of claim 13, wherein the ergonomic body comprises one or more grip features configured to contact at least a portion of a user's hand to facilitate gripping of the wireless camera by the user.

* * * * *